United States Patent
Chez

(10) Patent No.: US 10,039,808 B2
(45) Date of Patent: Aug. 7, 2018

(54) METHOD OF TREATING OR IMPROVING NEUROLOGICAL FUNCTION IN A HUMAN SUBJECT

(71) Applicant: Michael Chez, Granite City, CA (US)

(72) Inventor: Michael Chez, Granite City, CA (US)

( * ) Notice: Subject to any disclaimer, the term of this patent is extended or adjusted under 35 U.S.C. 154(b) by 0 days.

(21) Appl. No.: 14/886,231

(22) Filed: Oct. 19, 2015

(65) Prior Publication Data

US 2016/0228510 A1    Aug. 11, 2016

Related U.S. Application Data

(60) Provisional application No. 62/067,226, filed on Oct. 22, 2014.

(51) Int. Cl.
| | |
|---|---|
| A61K 38/00 | (2006.01) |
| A61K 39/00 | (2006.01) |
| A61K 45/00 | (2006.01) |
| A61K 38/19 | (2006.01) |
| A61K 38/18 | (2006.01) |
| G01N 33/68 | (2006.01) |
| A61K 9/00 | (2006.01) |

(52) U.S. Cl.
CPC .......... *A61K 38/193* (2013.01); *A61K 9/0019* (2013.01); *A61K 38/18* (2013.01); *G01N 33/6863* (2013.01); *G01N 33/6869* (2013.01); *G01N 33/6893* (2013.01)

(58) Field of Classification Search
None
See application file for complete search history.

(56) References Cited

U.S. PATENT DOCUMENTS

| | | | |
|---|---|---|---|
| 7,456,224 B2 | 11/2008 | Chez | |
| 7,695,723 B2 * | 4/2010 | Schaebitz | A61K 38/1816 424/198.1 |
| 7,709,213 B2 | 5/2010 | Chez | |
| 7,785,601 B2 | 8/2010 | Schaebitz et al. | |
| 8,084,421 B2 | 12/2011 | Lopez et al. | |
| 8,236,306 B2 | 8/2012 | Tobinick | |
| 8,354,438 B2 | 1/2013 | Chez | |
| 8,372,397 B2 | 2/2013 | Moon et al. | |
| 8,431,538 B2 | 4/2013 | Kozikowski | |
| 8,524,655 B2 | 9/2013 | Zhao et al. | |
| 8,545,812 B2 | 10/2013 | Hong et al. | |
| 8,613,929 B2 | 12/2013 | Gaillard et al. | |
| 8,741,847 B2 | 6/2014 | Chez | |
| 2002/0198150 A1 | 12/2002 | Chajut | |
| 2008/0292597 A1 | 11/2008 | Steenblock | |
| 2011/0060266 A1 | 3/2011 | Streeter et al. | |
| 2011/0104100 A1 | 5/2011 | Riordan et al. | |
| 2012/0231065 A1 | 9/2012 | Schaebitz et al. | |
| 2013/0028870 A1 | 1/2013 | Royal et al. | |
| 2013/0281484 A1 | 10/2013 | Kozikowski et al. | |
| 2014/0005071 A1 | 1/2014 | Chappell et al. | |
| 2014/0056842 A1 | 2/2014 | Sackner-Bernstein et al. | |
| 2014/0065162 A1 | 3/2014 | Lipson et al. | |

FOREIGN PATENT DOCUMENTS

| | | |
|---|---|---|
| EP | 2 186 252 A2 | 5/2010 |
| WO | 2003061685 A1 | 7/2003 |
| WO | 2008031448 A1 | 3/2008 |
| WO | 2010051335 A1 | 5/2010 |

OTHER PUBLICATIONS

Boussi-Gross, et al.: "Hyperbaric Oxygen Therapy Can Improve Post Concussion Syndrome Years after Mild Traumatic Brain Injury," Randomized Prospective Trial, Plos One, Nov. 2013, vol. 8, No. 11.
English Abstract of WO 2003061685.
Gardellini, A., et al., "Filgrastim XM02 (Tevagrastim) after autologous stem cell transplantation compared to lenograstim: favourable cost-efficacy analysis," Ecancer Medical Science, Jun. 25, 2013.
Chez, et al.: "Immune Therapy in Autism: Historical Experience and Future Directions with Immunomodulatory Therapy," Neurotherapeutics: The Journal of the American Society for Experimental NeuroTherapeutics, Jul. 2010, 293-301, vol. 7.
Jensen, et al.: "First Autologous Cell Therapy of Cerebral Palsy Caused by Hypoxic-Ischemic Brain Damage in a Child after Cardiac Arrest—Individual Treatment with Core Blood," Case Reports in Transplantation, 2013.
Grigg, AP.,: "Optimizing dose and scheduling of filgrastim (granulocyte colony-stimulating factor) for mobilization and collection of peripheral blood progenitorcells in normal volunteers," Blood, 1995, 4437-4445, 86.
Connolly, A., et al.: "Brain-Derived Neurotrophic Factor and Autoantibodies to Neural Antigens in Sera of Children with Autistic Spectrum Disorders, Landau-Kleffner Syndrome, and Epilepsy," Society of Biological Psychiatry, 2005.
Chez, M., Md., : "Autologous Umbilical Cord Blood Treatment for Autism: Rationale and Potential Goals of Treatment," Practical Neurology, 2013.
Jensen, A.,: "Autologous Cord Blood Therapy for Infantile Cerebral Palsy: From Bench to Bedside," Obstetrics and Gynecology International, 2014, vol. 2014.
Sun, J., et al.: "Cord blood for brain injury," Cytotherapy, 2015, 1-11.
Papadopoulos, K., et al.: "Safety and feasbility of autologous umbilical cord blood transfusion in 2 toddlers with cerebral palsy and the role of low dose granulocyte-colony stimulating factor injections," Restorative Neurology and Neuroscience, 2011, 17-22, vol. 29.
"Cord Blood for Cerebral Palsy: 1st publication of controlled trial," Parent's Guide to Cord Blood Foundation, Dec. 24, 2012.

(Continued)

*Primary Examiner* — Olga N Chernyshev
(74) *Attorney, Agent, or Firm* — Cahn & Samuels, LLP

(57) ABSTRACT

A method of treating or improving neurological function in a human subject includes identifying a human subject diagnosed with at least one of post-CNS trauma, post-concussion syndrome, a chronic refractive epileptic encephalopathic condition, autism spectrum condition, cerebral palsy; or ischemic long term treatment for remote ischemic or traumatic brain injury; and administering to the human subject a composition comprising a pharmaceutically effective dose of filgrastim.

12 Claims, No Drawings

(56) References Cited

OTHER PUBLICATIONS

Lv, Y., et al.,: "Transplantation of human cord blood mononuclear cells and umbilical cord-derived mesenchymal stem cells in autism," Journal of Translational Medicine, 2013, 11:196.

Chez, M., et al.: "Safety and Observations in a Pilot Study of Lenalidomide for Treatment in Autism," Autism Research and Treatment, 2012, vol. 2012.

PCT Application PCT/US15/56299, Notification of Transmittal of the International Search Report and the Written Opinion of the International Searching Authority, or the Declaration, dated Jan. 6, 2016.

Connolly, A., et al.: "Serum autoantibodies to brain in Landau-Kleffner variant, autism, and other neurologic disorders," The Journal of Pediatrics, May 1999, 607-613, vol. 134, No. 5, Mosby, Inc.

Min, K., et al.: "Umbilical Cord Blood Therapy Potentiated with Erythropoietin for Children with Cerebral Palsy: A Double-blind, Randomized, Placebo-Controlled Trial," Stem Cells, Mar. 2013, 31(3), 581-91.

Neupogen Administration Guidelines from Amgen, 43 pages revised 2016.

\* cited by examiner

METHOD OF TREATING OR IMPROVING NEUROLOGICAL FUNCTION IN A HUMAN SUBJECT

This application claims priority to U.S. Ser. No. 62/067,226 filed on 22 Oct. 2014 in the United States Patent and Trademark Office, the entirety of which is incorporated herein by reference.

FIELD OF INVENTION

Filgrastim (e.g., commercially available from Amgen Inc. as NEUPOGEN®, and other biological filgrastim generics that may be made by others, such as Novartis, Sanofi, and other manufacturers as biosimilar), derivatives, and pharmaceutically effective salts thereof may offer renewable, autologous stem cell release; possible autologous neuronal endogenous stem cell activation; and/or peripheral and central nervous system (CNS) glial neuroimmune modulation effects. One or more of these mechanisms may lead to treatment and improvement in at least one of the following conditions: chronic post-traumatic inflammation in post-CNS trauma victims, post-concussion syndrome, epileptic encephalopathic conditions, autism spectrum conditions, as well as chronic cerebral palsy.

BACKGROUND OF INVENTION

Filgrastim is a hematological growth factor that can release neutrophils and autologous stem cells from the bone marrow of an individual. These can maximize in 4-5 days after daily subcutaneous injection (Grigg et al., Blood 1995, (86): 4437-4445) and create circulating stem and immune cells that can be harvested.

Examples in animal studies suggest reimplantation or reinfusion of stem cells in neurological conditions like acute stroke or trauma. These studies have been done with umbilical cord blood as well as donor stem cells from fetal animals or cultures. Some animal models of acute stroke have tried this with mixed results, and a brief human trial did not show significance that was seen in animal models, mainly in rats (Moriya et al., J. Stroke Cerebrovasc Dis. 2013 October; 22(7):1088-97). This animal work is reflected in U.S. Pat. No. 7,785,601 for animal models of Parkinson's disease.

WO2008/031448A1 discloses extraction and growing of stem cells with filgrastim preparation. U.S. Pat. No. 8,524,655 shows animal use for acute ischemia after 3-4 hours of injury. However, this does not reflect chronic long term damage perhaps weeks, months, or years later.

In a few human acute stroke studies there are limited data suggesting some mild trend to improve by using reinfused hematological peripheral stem cells, but changes in clinical imaging or length of hospital stay have not been found. Filgrastim has been used without harvesting in acute models of animal and human stroke patients. In controlled human studies designed for acute ischemic damage, 150-300 microgram per Kg of filgrastim did initially, in acute stroke, cause some improvement and was shown to have no major adverse effect from injection (Moriya et al, 2013; Shyu et al. 2006). However, in a larger controlled trial (128 microgram/Kg in acute stroke vs control in 328 patients), there were no objective changes seen between injection group and controls to really change post-stroke outcome (Ringelstein et al., 2013).

In chronic brain injury after head trauma, there is evidence that chronic inflammatory changes may persist, and cause long term progression and lack of regaining new neuronal connections and functional improvement. In acute concussion and post-concussion syndrome there may also be residual glial activation in the CNS that promotes chronic inflammation. Peripheral White Blood Cell Count (WBC) with neutrophils are especially able to modify or influence the state of inflammation in a given individual, as stem cells released may down regulate an overly-activated pro-inflammatory state. Glial CNS activation may be modified from peripheral immune factors, which peripheral hematological stem cells released by filgrastim may produce.

Applicant has written articles on and obtained patents directed to inflammatory cytokines, immune mechanism, and treatment options for pervasive development disorders, such as epilepsy, autism, and autism spectrum conditions. See, e.g., U.S. Pat. Nos. 7,456,224; 7,709,213; 8,354,438; and 8,741,847. The entireties of these U.S. patents are incorporated herein by reference. Further, Applicant has extensive research in conditions related to inflammation in form of cytokine and other pro-inflammatory agents (e.g., such as tumor necrosis factor TNF-α, TNF-β, interleukin IL-1a, IL-1b, IL-13, IL-6, and IL-10) as well as similar mechanisms involving neuronal CNS inflammation driven by chronic glial inflammatory response post-injury.

SUMMARY OF INVENTION

According to at least one embodiment of the present invention, a method of treating or improving neurological function in a human subject is provided. A human subject diagnosed with at least one of post-CNS trauma, post-concussion syndrome, a chronic refractive epileptic encephalopathic condition, autism spectrum condition, cerebral palsy; or remote ischemic or traumatic brain injury is identified. A composition comprising a pharmaceutically effective dose of filgrastim is administered to the human subject. The composition comprises no stem cells and no bone marrow suppression agent.

According to another embodiment of the present invention, the human subject is diagnosed with post-CNS trauma or post-concussion syndrome and administration of the composition is at least one week to one year after an initial trauma or concussion.

According to another embodiment of the present invention, after administration of the composition the human subject's motor function, speech function, or social skills are measured.

According to yet another embodiment of the present invention, a method of treating or improving neurological function in a human subject comprising identifying a human subject with a neurological condition due to inflammation from cytokines and/or due to a chronic glial response to remote injury and cell death; and administering to the human subject a composition comprising a pharmaceutically effective dose of filgrastim.

According to another embodiment of the present invention, the neurological condition is identified by an elevated level of at least one of tumor necrosis factor TNF-α, TNF-β, interleukin IL-1a, IL-1b, IL-13, IL-6, IL-10, or any combination thereof as compared to a level in a normal human subject without any neurological condition or injury.

An advantage of the methods of the present invention is that they are less costly, being about 5-10 times less expensive, than a simple stem cell infusion at a typical U.S. medical center. The methods require no stem cell donor, or immunosuppression, or risk of graft versus host disease.

DETAILED DESCRIPTION OF INVENTION

Autoimmune or chronic inflammatory conditions include, but are not limited to, chronic post-traumatic inflammation in post-CNS trauma victims, post-concussion syndrome, epileptic encephalopathic conditions, autism spectrum conditions, and cerebral palsy.

Epileptic encephalopathic conditions may include, but are not limited to, Lennox Gastaut syndrome, Landau Kleffner Syndrome, infantile spasms, Dravet Syndrome, and other epileptic encephalopathies where a chronic CNS process evolving into cell death as part of a chronic remote injury may yield a chronic CNS type inflammatory glial or similar response. Autism spectrum conditions or disorders may include, but are not limited to, pervasive development disorder (PDD-NOS), autism, and Asperger's.

According to the present invention, the above conditions may benefit from treatment with a composition comprising a pharmaceutically effective dose of filgrastim, a derivative thereof, or a pharmaceutically effective salt thereof. In a specific embodiment, the present invention is directed to treatment of chronic inflammatory states from remote CNS injury in otherwise non-progressive conditions and to treatment of acute or subacute conditions, for example, ischemia or trauma.

Any effective pharmaceutical preparation or administration of the composition may be used (e.g., as a tablet, capsule, injection, inhalant, or strip). In a preferred embodiment, the treatment comprises an injection. In a specific embodiment, One or more peripheral injections of subcutaneous filgrastim may offer improvement in a patient having remote persisting symptoms of traumatic brain injury, long after stroke or acute insult is resolved and the patient becomes chronically stabilized in a post-injury state. In a specific embodiment the administration may occur at least one week, at least three months, at least 6 months, at least one year, or at least two years after an initial trauma, brain injury, or concussion.

In embodiments, the composition may comprise about 10-10,000 µg, for example about 50-1,000 µg, or about 100-500 µg, of filgrastim, a derivative thereof, or a pharmaceutically effective salt thereof. The administration may be daily (e.g., for 3-5 days in a course and may be repeated based on clinical findings), weekly, bimonthly, quarterly, or biannually as long as a clinically useful response occurs. A clinically useful response may be defined as an improvement or gain in at least one functional change from a chronically impaired or lost functional skill. This response may be an objective change in motor function or mobility; speech function in receptive and/or expressive speech standardized scores; cognitive or mental function; behaviors or daily living skills (e.g., in autism, trauma, cerebral palsy); or improved headache or inflammation (e.g., post-concussion), among other measurable improvement goals depending on condition. In epilepsy, a clinically useful response may be defined as improved cognitive or daily living skills and most importantly reduced seizure frequency and/or severity.

According to the present invention, the composition contains no stem cells; no processed external stem cells; no enrichment of a stem cell harvest; no stem cell reinfusion; and no bone marrow suppression or other agents that may be typically used in oncology or hematology. Because the released stem cells are autologous, Applicant believes that safety is evident in prior studies and there is no risk of graft vs. host disease. In a specific embodiment, CD34+ and CD45− cells can be measured to estimate autologous stem cells produced by the present invention, so that dosing can be determined without extracting cells and reimplanting or infusing.

One mechanism of filgrastim treatment according to the present invention may comprise renewable, autologous stem cell release; possible autologous neuronal endogenous stem cell activation; peripheral and central nervous system (CNS) glial neuroimmune modulation effects; or a combination thereof. Another mechanism of filgrastim treatment may affect CNS residual stem cells through possible GCSF receptors on innate autologous neuronal stem cells through GCSF receptor activation. Other possible mechanisms may involve peripheral autologous release of hemapoetic stem cells that modify B and T cells interacting to modulate innate glial and other brain immune processes, such as reducing pro-inflammatory cytokine levels or interfacing at blood brain barrier to modify glial cell inflammation. Autoantibody T-cell production may be inhibited as well.

The present invention is different from the known art as demonstrated by actual clinical evidence in appropriate patients. In a specific embodiment, Applicant injected a patient (for 4-5 days for 2 courses) with filgrastim at 300 micrograms daily without harvesting cells. Applicant demonstrated maximal tripling or quadrupling of neutrophils in clinical complete blood counts (CBC) in a 9 year old male patient, 3 years post-severe CNS trauma. This patient clinically improved within 2-4 weeks with improved motor function, head control, and volitional movements of lower and upper extremities.

A second patient (21 year old female) had chronic neutropenia from medications for autism and seizure disorder. Her speech and socialization were better after 4 days of filgrastim injections and elevation doubling to tripling her WBC and increased her ANC from 1000 to 4200. Therefore, in chronic autism and remote ischemia and traumatic injury to the brain, the present invention shows improvement time linked within 2-4 weeks post filgrastim injections without harvesting or enriching the autologous cells and reinjecting them as other uses in clinical medicine typically do, such as hematological rescue efforts after chemotherapy or grafting for bone marrow replacement.

A third patient (4 year old male) with autism had dramatic response to an autologous cord blood infusion improving receptive speech. Therefore, compassionate use of filgrastim injection was given for 2 courses of 5 days each. There was a dramatic increase from 9000 WBC to 64,000 WBC and increase in CD34 component tripled correlating with stem cell release from bone marrow following filgrastim treatment. CBC was done before, at midpoint ($3^{rd}$ day), $5^{th}$ day, and post infusions. Within days, the patient had expressive speech and improved performance in school and was able to expressively put two and three words together and improved on receptive speech, even more than with initial cord blood stem cell infusion.

EXAMPLES

The following non-limiting examples are illustrative of the present invention showing a response to treatment with a composition comprising filgrastim.

Patient 1: Head Trauma

Patient 1, a 10 year old male, had head trauma and subsequent diffuse multifocal brain injury. The patient was quadriparetic with asymmetric muscle tone. The patient was unable at baseline to hold head against gravity, unable to volitionally initiate or sustain leg stepping movements, and also unable to crawl on all four extremities at over 3 years post-injury.

The patient was treated with two series of filgrastim injections (NEUPOGEN®): 1) the first injection comprised 300 ug per day for 5 days for weight of 30 KG for patient), and 2) the second injection comprised the same dosage for 3 days and was administered 4 months after the first series of filgrastim injections.

The patient exhibited crawling, pushing to lift his torso against gravity, and in-harness increased stepping. This was after first series of injection. The second series led to leg stepping and increased trunkal antigravity function, volitional increase arm movements and head control along with attempted vocalizations. The patient showed improved ability to hold his head up against gravity for longer periods and have increased use of both upper and lower extremities as measured by therapy notes from physical therapy, a patient log, and videotaping to observe and note changes. No regression or loss of improvement has occurred 12 months post first injection 8 months post second injection.

These improvements occurred within the first 2 weeks after each infusion series ended. The patient has improved in awareness and strength (as demonstrated by physical therapy notes and video). The patient was receiving the same physical therapy protocol from same therapist most of the past 3 years and no other major new treatments were introduced.

Complete Blood Count (CBC) and liver functions were stable after the second treatment as determined by venous blood testing. After the first treatment, the patient showed a drop in platelets transiently, but this improved after stopping treatment. White blood cell (WBC) were elevated with left shift of neutrophils rising from 2200 ANC to 7600 ANC and total WBC increase from 4800 to 18000. The WBC returned to baseline within a few days.

Improvement in Patient 1 had occurred previously over 18 months before, with slight new volitional hand movements, after his autologous cord blood was intravenously given, but only enough stem cells from umbilical cord blood for one (1) infusion limited treatment. Because of prior history of responding to an autologous umbilical cord blood stem cell compassionate use infusion, the prescription of filgrastim injection was considered and recommended as low risk. The child had some intermittent drug-induced neutropenia as well which filgrastim could help treat.

The patient continued improving. Strengthening of his leg volitional movements and head control has continued to improve. The patient has improved in awareness and strength. He now cries when in pain and is more aware and interactive with family and caregivers. He continue to make progress in motor skills since both infusions, where he was stagnant in gains before.

Patients 2-3: Autism

Patient 2 was a 21 year old female with autism. Patient 3 was a 4 year old male.

Patient 2 was treated with two series of filgrastim injections: 1) for 4 days by administering 300 ug of NEUPOGEN® via subcutaneous injection, and 2) another 3 day course at the same dosage 2 months after completion of the first series of administration. Patient 3 had two courses 300 ug NEUPOGEN® via subcutaneous injection separated by 4 months between treatments. These were 5 day courses each.

Patient 2 seemed to process better and was more social, showing responsiveness to verbal communication initiation and according to caregiver observation notes. Improved communication was seen by increased verbal output and response to commands.

Patient 3 started saying expressive speech single words for first time and improved on receptive speech drills with his ABA providers. After second treatment course, Patient 2 was showing more behavioral compliance, while Patient 3 showed putting more than single words together and being more engaged socially and sought out playing with peers and taking turns in play therapy games, demonstrating shared interest with therapist and parent for first time. These are significant core problems being improved by filgrastim product treatments.

Patient 2 motor improvement was less dramatic than Patient 1, as motor function was not as abnormal. Communication and social improvement in both Patient 2 and Patient 3 were seen. Patient 2 had response to prednisone after autism regression as a child and had a history of epilepsy, which may cause chronic inflammatory state in CNS. She also had cycles of psychiatric deterioration responsive in the past to prednisone and lenolanamide (REVLIMID®) suggesting some immunological component to her condition. She has family history of rheumatoid arthritis. She has to date no known genetic condition with exome and microarray and specific genetic probe testing. Patient 3 has maternal autoimmune condition in pregnancy and clear immunological regressions after illness historically. His response to treatments was dramatic for communication receptively, but for the first time expressively improving more after second treatment.

The above demonstrates that injections of filgrastim (e.g., for 3-5 days) subcutaneously results in clinical improvement of core symptoms in patients with remote residual head trauma or chronic encephalopathic quadriparetic and improved language processing.

Accordingly, in view of the above data, there may be inflammatory driven conditions (e.g., post-concussion syndrome) that responds to treatment with filgrastim. This may be cytokine driven as well in the CNS in form of chronic glial response to remote injury and cell death. Chronic post traumatic brain injury cases and some cerebral palsy cases tend to get worse over time. These may be due also to chronic inflammation, as researchers have found relationship in animal and human models showing elevated pro-inflammatory markers in brain or CSF of subjects studied.

Whether a direct immune effect on cytokines or other cellular driven immune activity, or actual CNS stem cell activation and repair over time, the clinical evidence in the above three human candidates demonstrates improvement time-linked with these treatments.

Thus, the present invention may open new methodology for treatment of disease where stem cell mobilization may yield direct or indirect neurological function in untreatable conditions. The present invention does not grow out or harvest and enrich or modulate the bone marrow stem cells released by filgrastim. Measurements are easy to estimate clinically based on subsets of neutrophils like CD34+ and CD45− percentages in peripheral venous blood tests commonly available. Cytokine measurements in blood or CSF samples could also be measured pre- and post-injections. In addition, no matched or autologous supply of stem cells from bone marrow, tissue, cord blood, or other sources externally are needed which allows greater and immediate treatment early in the course of above disease processes.

The addition of filgrastim or filgrastim agents may also augment or be beneficial as co-treatment, pre-treatment, or post-treatment as an augmentation to other stem cell therapy models, extending or enhancing any external stem cell infusions that offer beneficial clinical response. This may offer maintenance boosting of stem cell therapy response as well with post-treatment interval treatments with a filgrastim agent especially when the stem cell therapy is in short supply or hard to obtain.

As used herein "substantially", "generally", "relatively", "approximately", and "about" are relative modifiers intended to indicate permissible variation from the characteristic so modified. It is not intended to be limited to the absolute value or characteristic which it modifies but rather approaching or approximating such a physical or functional characteristic.

References to "one embodiment", "an embodiment", or "in embodiments" mean that the feature being referred to is included in at least one embodiment of the invention. Moreover, separate references to "one embodiment", "an embodiment", or "in embodiments" do not necessarily refer to the same embodiment; however, neither are such embodiments mutually exclusive, unless so stated, and except as will be readily apparent to those skilled in the art. Thus, the invention can include any variety of combinations and/or integrations of the embodiments described herein.

Although specific embodiments of the invention have been described herein, it is understood by those skilled in the art that many other modifications and embodiments of the invention will come to mind to which the invention pertains, having benefit of the teaching presented in the foregoing description and associated drawings.

It is therefore understood that the invention is not limited to the specific embodiments disclosed herein, and that many modifications and other embodiments of the invention are intended to be included within the scope of the invention. Moreover, although specific terms are employed herein, they are used only in generic and descriptive sense, and not for the purposes of limiting the description invention.

What is claimed is:

1. A method of treatment, comprising:
   identifying a human subject diagnosed with an autism spectrum disorder; and
   administering to the human subject a composition comprising a therapeutically effective dose of filgrastim, wherein said composition comprises no stem cells and no bone marrow suppression agent.

2. A method according to claim 1, wherein the administering is via injection of the composition.

3. A method according to claim 1, wherein the pharmaceutically effective dose comprises about 100-10,000 micrograms of filgrastim.

4. A method according to claim 1, wherein said method comprises no harvesting, reimplantation, or reinfusion of stem cells.

5. A method according to claim 1, wherein no pretreatment for immunosuppression is provided.

6. A method according to claim 1, wherein said composition comprises no blood.

7. A method according to claim 1, further comprising measuring the human subject's motor function, speech function, or social skills after said administering.

8. A method according to claim 1, wherein the autism spectrum disorder comprises pervasive development disorder, autism, or Asperger's.

9. A method for treatment, comprising:
   identifying a human subject diagnosed with at least one of post-CNS trauma, post-concussion syndrome, or traumatic brain injury; and
   administering to the human subject a composition comprising a therapeutically effective dose of filgrastim, wherein said composition comprises no stem cells and no bone marrow suppression agent,
   wherein a first administering of the composition is at least 6 months after an initial trauma, brain injury, or concussion.

10. A method according to claim 9, wherein a first administering of the composition occurs at least 1 year after an initial trauma, brain injury or concussion.

11. A method according to claim 9, wherein a first administering of the composition is at least 2 years after an initial trauma, brain injury, or concussion.

12. A method according to claim 9, wherein the human subject has remote persisting symptoms of traumatic brain injury at least one year after an initial trauma or concussion, and the human subject is chronically stabilized in a post-injury state.

* * * * *